United States Patent [19]

Horikawa et al.

[11] Patent Number: 5,260,438
[45] Date of Patent: Nov. 9, 1993

[54] METHOD FOR REMOVING THE PROTECTING GROUP FOR HYDROXY GROUP

[75] Inventors: Hiroshi Horikawa, Kawanishi; Kazuhiko Kondo, Osaka; Tameo Iwasaki, Nishinomiya, all of Japan

[73] Assignee: Tanabe Seiyaku Co., Ltd., Osaka, Japan

[21] Appl. No.: 52,680

[22] Filed: Apr. 27, 1993

[51] Int. Cl.$^5$ ............... C07D 487/00; C07D 499/00; C07D 487/08; C07D 487/04
[52] U.S. Cl. .................... 540/302; 540/310; 540/347; 540/350
[58] Field of Search ............ 540/302, 310, 347, 350

[56] References Cited

U.S. PATENT DOCUMENTS 4,174,316  11/1979  Christensen et al. .

FOREIGN PATENT DOCUMENTS

| | | |
|---|---|---|
| 0474243 | 6/1991 | European Pat. Off. . |
| 0105686 | 1/1980 | Japan . |
| 0069586 | 5/1980 | Japan . |
| 0123182 | 7/1982 | Japan . |
| 0103358 | 6/1983 | Japan . |
| 0202886 | 10/1985 | Japan . |
| 0233077 | 11/1985 | Japan . |
| 0005081 | 1/1986 | Japan . |
| 0103084 | 5/1987 | Japan . |
| 0054427 | 11/1987 | Japan . |
| 0079147 | 3/1989 | Japan . |
| 0000396 | 1/1991 | Japan . |
| 0014679 | 3/1992 | Japan . |

OTHER PUBLICATIONS

S. Hanessian, D. Desilets, Y. Bennani, "A Novel Ring--Closure Strategy for the Carbapenems: The Total thesis of (+)-Thienamycin", J. Org. Chem., 55, 3098-3103 1990.

A. G. M. Barrett, S. Sakadarat, "Total Syntheses of Penicillanic Acid S,S-Dioxide and 6-Aminopenicillanic Acid Using (Benzyloxy)nitromethane", J. Org. Chem., 55, 5110-5117 1990.

M. Imuta, et al. "Carbapenem and Penem Antibiotics. VI. Synthesis and Antibacterial Activity of 2-Heteroaromatic-thiomethys and 2-Carbamoyloxymethyl 1-Methylcarbapenems", Chem. Pharm. Bull. 39(3) 663-671.

*Primary Examiner*—Marianne M. Cintins
*Assistant Examiner*—Rebecca Cook
*Attorney, Agent, or Firm*—Browdy and Neimark

[57] ABSTRACT

A method for removing tri-substituted silyl group from $\beta$-lactam compound having a tri-substituted silyl group-protecting hydroxy group, which comprises treating with an acid and a fluoride selected from alkali metal fluoride, alkaline earth metal fluoride and hydrogenfluoride of organic or inorganic amine, by which the tri-substituted silyl group can be easily and effectively removed under moderate conditions so that the desired compound can be obtained in high yield at low cost.

23 Claims, No Drawings

METHOD FOR REMOVING THE PROTECTING GROUP FOR HYDROXY GROUP

The present invention relates to a novel method for removing the protecting group for hydroxy group.

PRIOR ART

β-Lactam compounds having a hydroxy group have been known to be useful as an antimicrobial agent having excellent antimicrobial activity or an intermediate thereof. For instance, there are disclosed various β-lactam antimicrobials such as penem antimicrobials [cf. Japanese Patent Second Publication (Kokoku) No. 396/1991, Japanese Patent First Publication (Kokai) No. 105686/1980, Japanese Patent Second Publication (Kokoku) No. 14679/1992], carbapenem antimicrobials [cf. Japanese Patent First Publication (Kokai) No. 202886/1985, Japanese Patent First Publication (Kokai) No. 5081/1986, Japanese Patent First Publication (Kokai) No. 233077/1985, Japanese Patent First Publication (Kokai) No. 79147/1989, Japanese Patent First Publication (Kokai) No. 69586/1980, EP-A-474243], oxapenem antimicrobials [cf. Japanese Patent First Publication (Kokai) No. 103358/1983], carbacephem antimicrobials (cf. U.S. Pat. No. 4,174,316), and the like.

In the processes for preparing these conventional β-lactam antimicrobials, there are used intermediates having a protected hydroxy group, and such protecting groups for hydroxy group are tri-substituted silyl groups such as trimethylsilyl group, triethylsilyl group, t-butyldimethylsilyl group, t-butyldiphenylsiliyl group.

On the other hand, there have been known various methods for removing the above mentioned tri-substituted silyl groups, for example, 1) treating with tetra-n-butylammonium fluoride in the presence of acetic acid [cf. Journal of Organic Chemistry, Vol. 55, pp 3098–3103 (1990)], 2) treating with boron trifluoride ether complex in acetonitrile [cf. Japanese Patent Second Publication (Kokoku) No. 54427/1987], 3) treating with hydrochloric acid in methanol [cf. Japanese Patent First Publication (Kokai) No. 123182/1982], 4) treating with tetra-n-butylammonium fluoride in tetrahydrofuran [cf. Journal of Organic Chemistry, Vol. 55, pp 5110–5117 (1990)], 5) treating with aluminum chloride in anisole [cf. Chemical & Pharmaceutical Bulletin, Vol. 39, No. 3, pp 663–671 (1991)], and 6) treating with phosphate buffer (pH 3) in tetrahydrofuran [cf. Japanese Patent First Publication (Kokai) No. 103084/1987)], and the like. Among the above methods, methods 1), 2) and 3) are used for removal of t-butyldimethylsilyl group, and method 4), method 5) and method 6) are used for removal of t-butyldiphenyl silyl group, triethylsiliyl group and trimethylsilyl group, respectively.

However, in case that above mentioned tri-substituted silyl groups are removed from compounds having an unstable structure such as β-lactam compounds, the above mentioned conventional methods have various defects, for example, the yield of the product is low because the desired compound are decomposed during the reaction, or the removal of the protecting group is not completely accomplished, or the reagents used therefor are expensive.

BRIEF DESCRIPTION OF THE INVENTION

An object of the present invention is to provide a novel method for removing the protecting groups for hydroxy group. More particularly, the present invention provides a novel method for removing effectively tri-substituted silyl groups from a compound having a tri-substituted silyl group-protecting hydroxy group without decomposition of the desired product, even though the such compound has an unstable structure, such as β-lactam compounds.

DETAILED DESCRIPTION OF THE INVENTION

According to the present invention, the removal of the protecting group from a β-lactam compound having a tri-substituted silyl group-protecting hydroxy group is carried out by treating said β-lactam compound with a combination of a fluoride selected from a) an alkali metal fluoride, b) an alkaline earth metal fluoride, and c) a hydrogenfluoride with an inorganic or organic amine, and an acid.

The "fluoride" includes, for example, a) alkali metal fluorides such as potassium fluoride, sodium fluoride, cesium fluoride, etc., b) alkaline earth metal fluorides such as calcium fluoride, etc., c) hydrogenfluorides of an inorganic or organic amine such as ammonium fluoride, a tri-lower alkylammonium fluoride, a benzyl(di-lower alkyl)ammonium fluoride, pyridinium fluoride, etc.

The "acid" may be any strong or weak organic or inorganic acids, for example, lower alkanoic acids (e.g. acetic acid, propionic acid, butyric acid, etc.), hydroxy-substituted lower alkanoic acids (e.g. citric acid, etc.), trihalogeno-lower alkanoic acids (e.g. trifluoroacetic acid, etc.), lower alkanesulfonic acids (e.g. methanesulfonic acid, etc.), phenylsulfonic acids which may optionally be substituted by a lower alkyl group or a halogen atom (e.g. p-toluenesulfonic acid, benzenesulfonic acid, etc.), mineral acids (e.g. hydrofluoric acid, hydrobromic acid, sulfuric acid, hydrochloric acid, etc.), and the like.

The above mentioned fluorides and acids may be used in any form, for example, in the form of a mixture of a fluoride and an acid, or in the form of a compound consisting of these two components including a salt, a double salt, a complex, an adduct, etc.

The fluoride is used in an amount sufficient to remove the tri-substituted silyl group, for example, it is usually used in an amount of 1 to 10 equivalents, more preferably 4 to 8 equivalents to the starting compound. On the other hand, the amount of the acid varies according to acidity of the acid to be used, but it is usually used in an amount sufficient to keep the pH value of the reaction solution pH 2 to 7, preferably pH 4 to 7, for example, it is usually used in an amount of 0.01 to 10 equivalents, preferably 0.01 to 8 equivalents to the starting compound.

In case that a fluoride and an acid are used in the form of a mixture thereof, the fluoride is any one as mentioned above, but alkali metal fluorides, alkaline earth metal fluorides, and ammonium fluoride are preferable. The acid is any one as mentioned above, but lower alkanoic acids and mineral acids are preferable. The mixture of the fluoride and the acid is, for example, a mixture of an alkali metal fluoride and a lower alkanoic acid, a mixture of an alkaline earth metal fluoride and a lower alkanoic acid, and a mixture of ammonium fluoride and a mineral acid.

In case that the compound consisting of a fluoride and an acid is used, the compound may be any one which contains both a fluoride and an acid as a component, such as a compound wherein these two components act not independently but cooperatively in the reaction system, and a compound wherein said acid does not exist in the form of an acid in the reaction system. Suitable examples of the compound are compounds consisting of a fluoride selected from an alkali metal fluoride, an alkaline earth metal fluoride and a hydrogenfluoride of an inorganic or organic amine such as ammonium hydrogenfluoride ($NH_4F \cdot HF$) and alkali metal hydrogenfluorides [e.g. potassium hydrogenfluoride ($KF \cdot HF$), sodium hydrogenfluoride ($NaF \cdot HF$), etc.], and hydrogen fluoride. The compound is used in an amount wherein each component is contained in an amount as mentioned above, and the compound is preferably used in an amount of 1 to 10 equivalents, more preferably 4 to 8 equivalents to the starting compound.

The reaction can be carried out under cooling or with heating, for example, at 0° C., to 50° C., preferably at 15° C. to 25° C., in a solvent.

Although the solvent may be any one which does not affect the reaction, polar solvents are preferable. The polar solvent includes, for example, organic solvents such as dimethylformamide, acetonitrile, tetrahydrofuran, dimethylsulfoxide, dimethylacetamide, or a mixture of water and these organic solvents.

Moreover, in case that a mixture of an alkali metal fluoride or an alkaline earth metal fluoride and a lower alkanoic acid is used, the alkali metal fluoride or alkaline earth metal fluoride may be either in the form of an anhydride thereof or in the form of a hydrate thereof (e.g. potassium fluoride dihydrate). In case that a hydrate is used, the solvent used in the reaction is preferably a mixture of water and the above mentioned organic solvent, and water is used in an mount of 1 to 10 equivalents, preferably 2 to 8 equivalents to the alkali metal fluoride or alkaline earth metal fluoride.

In the present method, the $\beta$-lactam compound having a tri-substituted silyl group-protecting hydroxy group may be any conventional $\beta$-lactam compound, for example, a compound having a partial structure of the formula [I]:

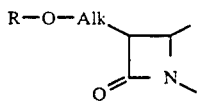

[I]

wherein R is a tri-substituted silyl group, and Alk is a straight chain or branched chain lower alkylene group, more particularly, a compound of the formula [I-a]:

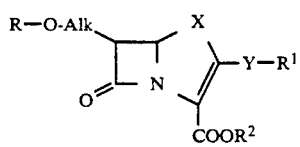

[I-a]

wherein $R^1$ is an organic group, a group of the formula: $-COOR^2$ is a protected or unprotected carboxyl group, X is a group of the formulae: $-CH_2CH_2-$, $-S-CH_2-$, $-O-CH_2-$, $-CH_2-$, $-CH(R^3)-$, $-S-$ or $-O-$, in which $R^3$ is a lower alkyl group, and Y is a sulfur atom, oxygen atom, or single bond, and R and Alk are the same as defined above.

The above mentioned $\beta$-lactam compounds are useful as antimicrobials, prodrugs thereof, or intermediate thereof.

The organic group represented by $R^1$ in the formula [I-a] may be any one which is used for conventional $\beta$-lactam antimicrobials, for example, lower alkyl groups, cycloalkyl groups, aryl groups (e.g. phenyl group, etc.), heterocyclic groups having at least one heteroatom selected from nitrogen atom, oxygen atom or sulfur atom (e.g. pyrrolidinyl group, piperidinyl group, furyl group, thienyl group, imidazolinyl group, pyridyl group, etc.), and the like. Besides, these groups may optionally have one or more substituents, and the substituent includes, for example, hydroxy group, a lower alkyl group, an amino-lower alkyl group, a lower alkoxy group, amino group, a lower alkylamino group, mercapto group, a lower alkylthio group, amidino group, guanidino group, carbamoyl group, thiocarbamoyl group, sulfamoyl group, carbamoyloxy group, cyano group, carboxyl group, a lower alkoxycarbonyl group, an aralkyloxycarbonyl group, oxo group, thioxo group, a halogeno group, a cycloalkyl group, an aryl group (e.g. phenyl group, etc.), a heterocyclic group (e.g. pyrrolidinyl group, piperidinyl group, furyl group, thienyl group, imidazolinyl group, pyridyl group, etc.), and the like.

In case that a group of the formula: $-COOR^2$ is a protected carboxyl group, the protecting group for the carboxyl group may be any conventional one, for example, groups which can be used for prodrugs of $\beta$-lactam antimicrobials, or groups which can be removed during the synthesis of $\beta$-lactam antimicrobials.

The groups which can be used for prodrugs of $\beta$-lactam antimicrobials are, for example, ester residues which are metabolized in living body by hydrolysis, and the like, for example, groups of the formulae: $-Z-O-COR^4$, $-Z-OCO_2R^4$ and $-Z-O-R^4$ (in which Z is a lower alkylene group, $R^4$ is a lower alkyl group, a cycloalkyl group, a lower alkenoyl group, a lower alkoxy-lower alkyl group, a lower alkanoyloxy-lower alkyl group). Suitable examples of these groups are a lower alkanoyloxy-lower alkyl group, a cycloalkylcarbonyloxy-lower alkyl group, a lower alkenoyloxy-lower alkyl group, a lower alkoxy-lower alkanoyloxy-lower alkyl group, a lower alkanoyloxy-lower alkoxy-lower alkyl group, a lower alkoxy-lower alkyl group, a lower alkoxy-lower alkoxy-lower alkyl group, a lower alkoxycarbonyloxy-lower alkyl group, a lower alkoxy-lower alkoxycarbonyloxy-lower alkyl group.

On the other hand, the groups which can be removed during the synthesis of $\beta$-lactam antimicrobials may be any conventional one, for example, a lower alkyl group, a lower alkenyl group, a halogeno-lower alkyl group, nitrobenzyl group, and a lower alkoxybenzhydryl group.

In the present invention, the "tri-substituted silyl group" used for protecting hydroxy group is silyl groups which are substituted by three groups selected from a straight chain or branched chain lower alkyl group and phenyl group, for example, tri-lower alkylsilyl groups (e.g. trimethylsilyl group, triethylsilyl group, etc.), branched chain lower alkyl group-substituted di-lower alkylsilyl groups (e.g. t-butyldimethylsilyl group, etc.), lower alkyl group-substituted di-branched chain lower alkylsilyl group (e.g. methyldiisopropylsilyl group, etc.), branched chain lower alkyl group-substituted diphenylsilyl groups (e.g. t-butyldiphenylsilyl group, etc.), and triphenylsilyl group. Among these groups, tri-substituted silyl group having 6 to 18 carbon atoms, especially, branched chain lower alkyl group-substituted di-lower alkylsilyl groups, lower alkyl group-substituted di-branched chain lower alkylsilyl groups, branched chain lower alkyl group-substituted diphenylsilyl group, triphenylsilyl group are preferable, and branched chain lower alkyl group-substituted di-lower alkylsilyl groups are more preferable.

Throughout the present invention, the "lower alkyl" group, the "lower alkylene group" and the "lower alkoxy group" are ones having 1 to 6 carbon atoms, preferably 1 to 4 carbon atoms, respectively. The "lower alkanoyl group" and the "lower alkenyl group" are ones having 2 to 7 carbon atoms, preferably 2 to 5 carbon atoms, respectively. The "lower alkenoyl group" and the "cycloalkyl group" are ones having 3 to 8 carbon atoms, preferably 3 to 6 carbon atoms, respectively. The "lower alkanoic acid" is ones having 2 to 7 carbon atoms, preferably 2 to 5 carbon atoms, and the "lower alkanesulfonic acid" is ones having 1 to 6 carbon atoms, preferably 1 to 4 carbon atoms.

EXAMPLES

The present invention is illustrated in more detail by the following Examples and Reference Examples, but should not be construed to be limited thereto.

EXAMPLE 1

A mixture of (1R,5S,6S)-2-[(4R)-pyrrolidine-3-thion-4-ylthio]-6-[(1R)-1-t-butyldimethylsilyloxyethyl]-1-methylcarbapen-2-em-3-carboxylic acid isobutyryloxymethyl ester (100 mg), dimethylformamide (2 ml), acetic acid (0.26 ml) and potassium fluoride.dihydrate (70 mg) is stirred at room temperature for three days. The mixture is evaporated under reduced pressure to remove the solvent, and to the residue is added ethyl acetate (10 ml). The mixture is washed, and evaporated under reduced pressure, and the resulting residue is purified by silica gel column chromatography (solvent; ethyl acetate) to give (1R,5S,6S)-2-[(4R)-pyrrolidine-2-thion-4-ylthio]-6-[(1R)-1-hydroxyethyl]-1-methylcarbapen-2-em-3-carboxylic acid isobutyryloxymethyl ester (54 mg) as syrupy crude product.

Yield: 76%.

Further, ethyl acetate is added to the above crude product, and thereto is further added diisopropyl ether to give (1R,5S,6S)-2-[(4R)-pyrrolidine-2-thion-4-ylthio]-6-[(1R)-1-hydroxyethyl]-1-methylcarbapen-2-em-3-carboxylic acid isobutyryloxymethyl ester (50 mg) as crystals.

M.p. 158°-159° C.

EXAMPLE 2

A mixture of (1R,5S,6S)-2-[(4R)-pyrrolidine-2-thion-4-ylthio]-6-[(1R)-1-t-butyldimethylsilyloxyethyl]-1-methylcarbapen-2-em-3-carboxylic acid allyl ester (1.00 g), dimethylformamide (10 ml) and ammonium hydrogenfluoride (459 mg) is stirred at room temperature for three days. To the reaction solution is added a phosphate buffer (pH 7.0), and the mixture is extracted with ethyl acetate. The organic layer is washed with a phosphate buffer, and the washing and the phosphate buffer layer are combined, and extracted with ethyl acetate. The organic layers are combined, washed, dried and concentrated under reduced pressure. The resulting residue is crystallized from a mixture of ethyl acetate and n-hexane (2:1) to give (1R,5S,6S)-2-[(4R)-pyrrolidine-2-thion-4-ylthio]-6-[(1R)-1-hydroxyethyl]-1-methylcarbapen-2-em-3-carboxylic acid allyl ester (657 mg). The filtrate of the above crystallization is concentrated under reduced pressure, and the residue is purified by silica gel flash column chromatography (solvent; chloroform:ethanol=30:1), and further crystallized from a mixture of ethyl acetate and n-hexane (2:1) to give (1R,5S,6S)-2-[(4R)-pyrrolidine-2-thion-4-ylthio]-6-[(1R)-1-hydroxyethyl]-1-methylcarbapen-2-em-3-carboxylic acid ally ester (24 mg).

Yield: 88.4%.

M.p. 144°-145° C.

EXAMPLE 3

A mixture of (1R,5S,6S)-2-[(4R)-pyrrolidine-2-thion-4-ylthio]-6-[(1R)-1-t-butyldimethylsilyloxyethyl]-1-methylcarbapen-2-em-3-carboxylic acid isobutyryloxymethyl ester (3 g), dimethylformamide (20 ml), N-methylpyrrolidone (7 ml) and ammonium hydrogenfluoride (1.21 g) is stirred at 20° C. for three days. The reaction mixture is poured into a phosphate buffer (pH 7.0), and the mixture is extracted with ethyl acetate. The aqueous layer is extracted with ethyl acetate, and the organic layers are combined, washed with water, dried, and concentrated under reduced pressure. The resulting residue is crystallized from a mixture of ethyl acetate and diisopropyl ether. To the resultant is added diisopropyl ether, and the precipitate is collected by filtration, and washed to give (1R,5S,6S)-2-[(4R)-pyrrolidine-2-thion-4-ylthio]-6-[(1R)-1-hydroxyethyl]-1-methylcarbapen-2-em-3-carboxylic acid isobutyryloxymethyl ester (2.17 g) as crystals.

Yield: 91.0%.

M.p. 158°-159° C.

EXAMPLE 4

The same procedures as Example 1 are repeated except that calcium fluoride is used instead of potassium fluoride to give (1R,5S,6S)-2-[(4R)-pyrrolidine-2-thion-4-ylthio]-6-[(1R)-1-hydroxyethyl]-1-methylcarbapen-2-em-3-carboxylic acid isobutyryloxymethyl ester.

EXAMPLE 5

The same procedures as Example 1 are repeated except that hydrobromic acid and ammonium fluoride are used instead of acetic acid and potassium fluoride to give (1R,5S,6S)-2-[(4R)-pyrrolidine-2-thion-4-ylthio]-6-[(1R)-1-hydroxyethyl]-1-methylcarbapen-2-em-3-carboxylic acid isobutyryloxymethyl ester.

EXAMPLE 6

The same procedures as Example 1 are repeated except that sulfuric acid and ammonium fluoride are used instead of acetic acid and potassium fluoride to give (1R,5S,6S)-2-[(4R)-pyrrolidine-2-thion-4-ylthio]-6-[(1R)-1-hydroxyethyl]-1-methylcarbapen-2-em-3-carboxylic acid isobutyryloxymethyl ester.

EXAMPLE 7

The same procedures as Example 2 are repeated except that potassium hydrogenfluoride is used instead of ammonium hydrogenfluoride to give (1R,5S,6S)-2-[(4R)-pyrrolidine-2-thion-4-ylthio]-6-[(1R)-1-hydroxyethyl]-1-methylcarbapen-2-em-3-carboxylic acid ally ester.

EXAMPLE 8

(3S,4S)-3-[(1R)-1-t-Butyldimethylsilyloxyethyl]-4-[(1S)-1-phenylthiocarbonylethyl]-1-(1-methoxycarbonylmethyl)-2-azetidinone is treated in the same manner as in Example 1, 2 or 3 to give (3S,4S)-3-[(1R)-1- hydroxyethyl]-4-[(1S)-1-phenylthiocarbonylethyl]-1-(1-methoxycarbonylmethyl)-2-azetidinone.

EXAMPLE 9–17

The compounds as listed in Table 1 are treated in the same manner as in Example 1, 2 or 3 to remove the t-butyldimethylsilyl group to give the corresponding de-silylated compounds.

TABLE 1

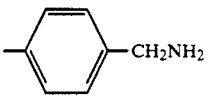

(TBS: t-butyldimethylsilyl group)

| Ex. No | X | Y | R¹ | R² |
|---|---|---|---|---|
| 9 | —CH(CH₃)— | Single bond |  | H |
| 10 | —CH(CH₃)— | Single bond | cyclopropyl-NH₂ | H |
| 11 | —CH(CH₃)— | Single bond | —CH₂-pyridyl | H |
| 12 | —CH(CH₃)— | S | N-methyl-thioxopyrrolidinyl | —CH₂OCOCH₃ |
| 13 | —CH₂— | S | —CH₂CH₂NH₂ | H |
| 14 | —S— | S | —CH₂CH₂OH | H |
| 15 | —O— | S | —CH₂CH₂NH₂ | H |
| 16 | —CH₂CH₂— | S | —CH₂CH₂NH₂ | H |
| 17 | —S— | Single bond | —CH₂OCONH₂ | —CH₂-C₆H₄-NO₂ |

EXAMPLES 18–21

The compounds as listed in Table 2 are treated in the same manner as in Example 1, 2 or 3 to remove the tri-substituted silyl group (R) to give the corresponding de-silylated compounds.

TABLE 2

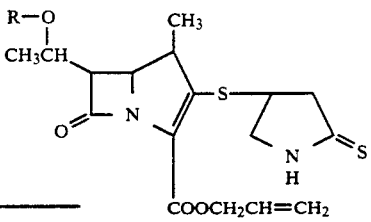

| Ex. No. | R |
|---|---|
| 18 | Triethylsilyl group |

TABLE 2-continued

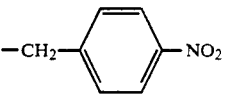

| Ex. No. | R |
|---|---|
| 19 | t-Butyldiphenylsilyl group |
| 20 | Methyldiisopropylsilyl group |
| 21 | Triphenylsilyl group |

REFERENCE EXAMPLE 1

(1) (3S,4S)-3-[(R)-1-t-Butyldimethylsilyloxyl]-4-[(1R)-1-carboxyethyl]-2-azetidinone (26.7 g) is suspended in acetonitrile (500 ml), and thereto is added carbonyldiimidazole (14.6 g). The mixture is stirred at room temperature for 30 minutes. To the reaction mixture is added mercaptomethylmalonic acid diethyl ester (20.3 g), and the mixture is stirred at room temperature for 20 minutes, and evaporated under reduced pressure to remove the solvent. To the residue is added diethyl ether (500 ml), and the mixture is washed, dried, and evaporated under reduced pressure. The residue is purified by silica gel column chromatography to give (3S,4S)-3-[(R)-1-t-butyldimethylsilyloxyethyl]-4-[(1R)-1-{2,2-bis(ethoxycarbonyl)ethylthiocarbonyl}ethyl]-2-azetidinone (33 g).

(2) The above product (1.4 g) and oxalic chloride isobutyryloxymethyl ester (0.64 g) are dissolved in dichloromethane, and thereto are added 2,6-lutidine (0.34 ml) and N,N-dimethylaminopyridine (10 mg) under ice-cooling, and the mixture is stirred at the same temperature for 30 minutes. To the reaction mixture are added oxalic chloride isobutyryloxymethyl ester (0.64 g) and 2,6-lutidine (0.34 ml), and the mixture is stirred for 30 minutes. The reaction mixture is poured into 0.1M phosphate buffer (pH 7) (100 ml), and extracted with dichloromethane. The extract is washed, dried, and evaporated under reduced pressure to remove the solvent. The resulting residue is purified by silica gel column chromatography to give (3S,4S)-3-[(R)-1-t-butyldimethylsilyloxyethyl]-4-[(1R)-1-{2,2-bis(ethoxycarbonyl)ethylthiocarbonyl}ethyl]-1-isobutyryloxymethyloxyoxalyl-2-azetidinone (1.7 g).

(3) The above product (1.7 g) is dissolved in a mixture of acetic acid (10 ml) and dichloromethane (10 ml), and thereto is added zinc (5 g) under ice-cooling, and the mixture is stirred for 30 minutes. The insoluble materials are removed by filtration on celite, and the filtrate is concentrated under reduced pressure. The residue is extracted with dichloromethane and the extract is washed, dried, and evaporated under reduced pressure to remove the solvent. The resulting residue is purified by silica gel column chromatography to give (3S,4S)-3-[(R)-1-t-butyldimethylsilyloxyethyl]-4-[(1R)-1-{2,2-bis(ethoxycarbonyl)ethylthiocarbonyl}ethyl]-1-[1-hydroxy-1-(isobutyryloxymethyloxycarbonyl)methyl]-2-azetidinone (1.5 g).

(4) To a solution of the above product (1.5 g) in tetrahydrofuran (10 ml) are added dropwise pyridine (0.21 ml) and thionyl chloride (0.24 ml) at −50° C., and the mixture is stirred at −50° to −40° C. for 30 minutes. The reaction mixture is diluted with ethyl acetate, and washed, and the organic layer is collected, dried, and evaporated to remove the solvent. The resulting residue; (3S,4S)-3-[(R)-1-t-butyldimethylsilyloxyethyl]-4-[(1R)-1-{2,2-bis(ethoxycarbonyl)ethylthiocarbonyl}ethyl]-1-(1-chloro-1-ethoxycarbonylmethyl)-2-azetidinone (0.8 g) is dissolved in dimethylformamide, and thereto is added triethylamine (0.34 ml) at −20° C., and the mixture is stirred at −20° to 0° C. for one hour. To the reaction mixture is added ethyl acetate (50 ml), and the mixture is washed. The organic layer is collected, dried, evaporated to remove the solvent, and the resulting residue is purified by silica gel column chromatography to give (5R,6S,7S)-7-[(R)-1-t-butyldimethylsilyloxyethyl]-5-methyl-4,8-dioxo-1-aza-4-thia-bicyclo[4.2.0]octane-2-carboxylic acid isobutyryloxymethyl ester (0.62 g).

(5) The above product (500 mg) and triphenylphosphine (277 mg) are dissolved in toluene (10 ml), and thereto is added t-butoxy potassium (130 mg) with stirring at −40° C. under nitrogen atmosphere. The mixture is stirred at the same temperature for 50 minutes. To the mixture is added dropwise a solution of diphenyl chlorophosphate (312 mg) in acetonitrile (10 ml) at −40° C., and the mixture is stirred for 40 minutes. To the reaction mixture are added (4S)-4-mercaptopyrrolidine-2-thione (155 mg) and isopropylethylamine (148 mg), and the mixture is stirred at −20° C. for 80 minutes, and further stirred at −5° C. for 90 minutes. The reaction solution is poured into 0.1M phosphate buffer (pH 7.0), and the mixture is extracted with ethyl acetate. The extract is washed, dried, and evaporated under reduced pressure to remove the solvent. The resulting residue is purified by silica gel column chromatography to give (1R,5S,6S)-2-[(4R)-pyrrolidine-2-thion-4-ylthio]-6-[(R)-1-t-butyldimethylsilyloxyethyl]-1-methylcarbapen-2-em-3-carboxylic acid isobutyryloxymethyl ester (248 mg).

REFERENCE EXAMPLE 2

(1) To a mixture of (3S,4S)-3-[(1R)-1-t-butyldimethylsilyoxyethyl]-4-(1R)-1-carboxyethyl]-2-azetidinone (10 g) and acetonitrile (50 ml) are added 4-dimethylaminopyridine (400 mg), t-butylmercaptan (5.98 g) and 1,3-dicyclohexylcarbodiimide (8.22 g) at −50° C. The mixture is stirred at room temperature for 17 hours, and the insoluble materials are removed by filtration, and the filtrate is concentrated under reduced pressure. Ethyl acetate is added to the residue, and the mixture is washed, dried and concentrated under reduced pressure. The residue is purified by silica gel column chromatography to give (3S,4S)-3-[(1R)-1-t-butyldimethylsilyloxyethyl]-4-[(1R)-1-t-butylthiocarbonyethyl]-2-azetidinone (11.7 g).

(2) To a mixture of the above product (320 mg), bromoacetic acid allyl ester (169 mg) and tetrahydrofuran (1 ml) is added dropwise 1M sodium bis(trimethylsilyl)amide (0.94 ml) in tetrahydrofuran at −65° C. to −60° C., and then, the mixture is warmed to −30° C. The reaction mixture is poured into water, and extracted with diethyl ether. The organic layer is washed, dried and concentrated under reduced pressure. The resulting residue is purified by silica gel column chromatography to give (3S,4S)-3-[(1R)-1-t-butyldimethylsilyloxyethyl]-4-[(1R)-1-t-butylthiocarbonylethyl]-1-(allyloxycarbonylmethyl)-2-azetidinone (538 mg).

(3) To a mixture of the above product (1 g) and tetrahydrofuran (6 ml) is added 1M solution of sodium bis(-trimethylsilyl)amide (4.24 ml) in tetrahydrofuran at −40° C. to −30° C. The mixture is stirred at −30° C. for 5 minutes, and thereto is added trimethylchlorosilane (230 mg) at −60° C. The mixture is stirred for 5 minutes, and thereto is added diphenylphosphoryl chloride (598 mg). The mixture is stirred at 0° C. for one hour, and the reaction solution is poured into a phosphate buffer (pH 7.0), and extracted with ethyl acetate. The extract is washed, dried, and concentrated under reduced pressure. The resulting residue is purified by reversed phase robber column (RP-8, manufactured by E. Merck) (solvent; acetonitrile:water=3:1) to give (1R,5R,6S)-6-[(1R)-1-t-butyldimethylsilyloxyethyl]-1-methyl-2-diphenylphosphoryloxy-carbapen-2-em-3-carboxylic acid allyl ester (1.1 g) as oil.

(4) To a mixture of the above product (100 mg) and acetonitrile (0.5 ml) are added (4R)-4-mercaptopyrrolidine-2-thione (22 mg) and diisopropylethylamine (21 mg) at 0° C. The mixture is stirred at 0° C. for one hour, and poured into a phosphate buffer (pH 7.0), and extracted with ethyl acetate. The extract is washed, dried, and concentrated under reduced pressure, and the residue is purified by silica gel column chromatography (solvent; n-hexane:chloroform:ethyl acetate=5:5:4) to give (1R,5S,6S)-2-[(4R)-pyrrolidine-2-thion-4-ylthio]-6-[(1R)-1-t-butyldimethylsilyloxyethyl]-1-methylcarbapen-2-em-3-carboxylic acid allyl ester (57 mg).

Effects of the Invention

According to the present invention, tri-substituted silyl groups are effectively removed under moderate conditions from a compound having tri-substituted silyl group-protecting hydroxy group, even though said compound has an unstable structure such as β-lactam compounds, so that the desired compound can be obtained easily and in high yield without decomposition of the desired compounds. Accordingly, the method of the present invention is industrially useful as a method for removing protecting groups for hydroxy group.

What is claimed is:

1. A method for removing a protecting group for hydroxy group from a β-lactam compound, which comprises treating said β-lactam compound having a tri-substituted silyl group-protecting hydroxy group with a fluoride selected from an alkali metal fluoride, an alkaline earth metal fluoride and a hydrogenfluoride of an inorganic or organic amine, and an acid.

2. The method according to claim 1, wherein the β-lactam compound having a tri-substituted silyl group-protecting hydroxy group is a compound having a partial structure of the formula [I]:

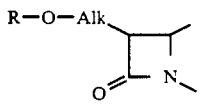

wherein R is a tri-substituted silyl group, and Alk is a straight chain or branched chain lower alkylene group.

3. The method according to claim 2, which comprises treating the β-lactam compound having a tri-substituted silyl group-protecting hydroxy group with a mixture of a fluoride selected from an alkali metal fluoride, an alkaline earth metal fluoride and a hydrogenfluoride of an inorganic or organic amine, and an acid.

4. The method according to claim 2, which comprises treating the β-lactam compound having a tri-substituted silyl group-protecting hydroxy group with a compound consisting of a fluoride selected from an alkali metal fluoride, an inorganic or organic amine, an hydrogen fluoride.

5. The method according to claim 1, wherein the β-lactam having a tri-substituted silyl group-protecting hydroxy group is a compound of the formula [I-a]:

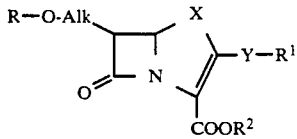

wherein R is a tri-substituted silyl group, R¹ is an organic group, a group of the formula: —COOR² is a protected or unprotected carboxyl group, Alk is a straight chain or branched chain lower alkylene group, X is a group of the formulae: —CH₂CH₂—, —S—CH₂—, —O—CH₂—, —CH₂—, —CH(R³)—, —S— or —O—, in which R³ is a lower alkyl group, and Y is a sulfur atom, oxygen atom or a single bond.

6. The method according to claim 5, which comprises treating the β-lactam compound having a tri-substituted silyl group-protecting hydroxy group with a mixture of a fluoride selected from an alkali metal fluoride, an alkaline earth metal fluoride and a hydrogenfluoride of an inorganic or organic amine, and an acid.

7. The method according to claim 5, which comprises treating the β-lactam compound having a tri-substituted silyl group-protecting hydroxy group with a compound consisting of a fluoride selected from an alkali metal fluoride, an inorganic or organic amine, an hydrogen fluoride.

8. The method according to claim 1, which comprises treating the β-lactam compound having a tri-substituted silyl group-protecting hydroxy group with a mixture of a fluoride selected from an alkali metal fluoride, an alkaline earth metal fluoride and a hydrogenfluoride of an inorganic or organic amine, and an acid.

9. The method according to claim 8, wherein the mixture of a fluoride and an acid is one selected from a mixture of an alkali metal fluoride and a lower alkanoic acid, a mixture of an alkaline earth metal fluoride with a lower alkanoic acid, and a mixture of ammonium fluoride and a mineral acid.

10. The method according to claim 1, which comprises treating the β-lactam compound having a tri-substituted silyl group-protecting hydroxy group with a compound consisting of a fluoride selected from an alkali metal fluoride, an alkaline earth metal fluoride and a hydrogenfluoride of an inorganic or organic amine, and hydrogen fluoride.

11. The method according to claim 10, wherein the compound consisting of a fluoride and hydrogen fluoride is an alkali metal hydrogenfluoride or ammonium hydrogenfluoride.

12. The method according to claim 1, wherein the tri-substituted silyl group is a silyl group which is substituted by three groups selected from a straight chain or branched chain lower alkyl group and phenyl group.

13. The method according to claim 1, wherein the tri-substituted silyl group is a tri-lower alkylsilyl group, a branched chain lower alkyl group-substituted di-lower alkylsilyl group, a lower alkyl group-substituted di-branched chain lower alkylsilyl group, a branched chain lower alkyl group-substituted diphenylsilyl group or a triphenylsilyl group.

14. The method according to claim 1, wherein the tri-substituted silyl group is a branched chain lower alkyl group-substituted di-lower alkylsilyl group.

15. The method according to claim 14, wherein the branched chain lower alkyl group-substituted di-lower alkylsilyl group is t-butyldimethylsilyl group.

16. A method for removing a tri-substituted silyl group from a β-lactam compound having a tri-substituted silyl group-protecting hydroxy group, which comprises treating said β-lactam compound with potassium fluoride and acetic acid in a polar solvent.

17. The method according to claim 16, wherein the tri-substituted silyl group is a silyl group which is substituted by three groups selected from a straight chain or branched chain lower alkyl group and phenyl group.

18. The method according to claim 16, wherein the tri-substituted silyl group is a tri-lower alkylsilyl group, a branched chain lower alkyl group-substituted di-branched chain lower alkylsilyl group, a branched chain lower alkyl group-substituted diphenylsilyl group or a triphenylsiyl group.

19. The method according to claim 16, wherein the tri-substituted silyl group is a branched chain lower alkyl group-substituted di-lower alkylsilyl group.

20. A method for removing a tri-substituted silyl group from a β-lactam compound having a tri-substituted silyl group-protecting hydroxy group, which comprises treating said β-lactam compound with ammonium hydrogenfluoride in a polar solvent.

21. The method according to claim 20, wherein the tri-substituted silyl group is a silyl group which is substituted by three groups selected from a straight chain or branched chain lower alkyl group and phenyl group.

22. The method according to claim 20, wherein the tri-substituted silyl group is a tri-lower alkylsilyl group, a branched chain lower alkyl group-substituted di-branched chain lower alkylsilyl group, a branched chain lower alkyl group-substituted diphenylsilyl group or a triphenylsiyl group.

23. The method according to claim 20, wherein the tri-substituted silyl group is a branched chain lower alkyl group-substituted di-lower alkylsilyl group.

* * * * *

UNITED STATES PATENT AND TRADEMARK OFFICE
CERTIFICATE OF CORRECTION

PATENT NO. : 5,260,438
DATED : November 9, 1993
INVENTOR(S) : Hiroshi HORIKAWA et al.

It is certified that error appears in the above-indentified patent and that said Letters Patent is hereby corrected as shown below:

Title page, column 1, between sections [22] and [51], insert:

```
    [30]        Foreign Application Priority Data
         Apr. 28, 1992 [JP] Japan...............154042/1992
         Oct. 27, 1992 [JP] Japan...............288605/1992
         Nov. 26, 1992 [JP] Japan...............317395/1992
```

Signed and Sealed this

Twenty-eighth Day of June, 1994

Attest:

BRUCE LEHMAN

Attesting Officer      Commissioner of Patents and Trademarks